United States Patent [19]

Vickery

[11] 4,277,475

[45] Jul. 7, 1981

[54] CONTRACEPTIVE METHODS EMPLOYING 1-SUBSTITUTED IMIDAZOLE DERIVATIVES

[75] Inventor: Brian H. Vickery, Cupertino, Calif.

[73] Assignee: Syntex (U.S.A.) Inc., Palo Alto, Calif.

[21] Appl. No.: 2,638

[22] Filed: Jan. 11, 1979

[51] Int. Cl.$^3$ .................. A61K 31/415; A61K 31/495
[52] U.S. Cl. ................................. 424/250; 424/273 R; 424/DIG. 14
[58] Field of Search ........................... 424/273 R, 250

[56] References Cited

U.S. PATENT DOCUMENTS

| 4,045,568 | 8/1977 | Walker | 424/273 R |
|---|---|---|---|
| 4,059,705 | 11/1977 | Walker | 424/273 R |
| 4,078,071 | 3/1978 | Walker | 424/273 R |

*Primary Examiner*—Leonard Schenkman
*Attorney, Agent, or Firm*—Kate H. Murashige; Alan M. Krubiner; Gerard A. Blaufarb

[57] ABSTRACT

1-Substituted imidazole derivatives exhibit spermatostatic and spermatocidal activity and are useful for contraceptive purposes both in male and female mammals.

19 Claims, No Drawings

CONTRACEPTIVE METHODS EMPLOYING 1-SUBSTITUTED IMIDAZOLE DERIVATIVES

BACKGROUND OF THE INVENTION

It has long been known that a variety of chemical agents when introduced into the vaginal canal as suitable compositions will interfere with mammalian spermatic cells and prevent their ability to effect conception either by reducing the motility of such cells (i.e. a spermatostatic effect) or by cytotoxicity (i.e. a spermatocidal effect). In general, the types of agents most widely used for such purpose are alkylphenoxypolyethoxyethanols, quaternary ammonium compounds and organomercurial compounds. Recently a series of 1,2-benzisothiazole derivatives having powerful spermatocidal activity were described in U.S. Pat. No. 4,093,730.

In general such spermatostatic and spermatocidal compounds for vaginal administration show little if any effect upon spermatic cells when administered systemically to the male mammal. Furthermore, for such systemic administration a compound must not only have powerful spermatostatic or spermatocidal activity but must show a low degree of toxicity to the host mammal.

It would, therefore, be desirable to have agents for contraceptive purposes which inhibit mammalian sperm cells from effecting conception (and possibly also prevent sperm cell production or maturation in the case of male contraception), which agents could be administered either intravaginally to the female mammal or systemically, preferably orally or via an implant, to the male mammal.

DESCRIPTION OF THE INVENTION

The present invention concerns methods of contraception and compositions therefor. More specifically, the present methods and compositions employ a large variety of 1-substituted imidazole derivatives, heretofore known as anti-fungal, anti-bacterial and anti-protozoal agents, as active ingredients exhibiting this surprising contraceptive utility. In particular, it has been found that this class of compounds interferes with mammalian spermatic cells and inhibits their ability to effect conception either by reducing their motility (spermatostatic activity) or by cytotoxicity (spermatocidal activity). These compounds are generally non-toxic to the host.

In one aspect the present invention is concerned with a method of contraception in a female mammal comprising administering intravaginally, to a subject clinically asymptomatic of vaginal microbial infection, prior to coitus, a spermatostatically effective amount of a 1-substituted imidazole, or salt thereof, or a pharmaceutical composition containing same.

In another aspect the present invention is concerned with pharmaceutical compositions for vaginal administration to a female mammal useful for practicing the aforementioned method.

In yet another aspect the present invention is concerned with a method of contraception comprising orally or parenterally (i.e., intramuscularly, intravenously or subcutaneously) administering, to a male mammal clinically asymptomatic of microbial infection, prior to coitus, a spermatostatically effective amount of a 1-substituted imidazole, or salt thereof, or a pharmaceutical composition containing same.

In yet another aspect the present invention concerns pharmaceutical compositions for oral or parenteral administration to a male mammal, useful for practicing the aforementioned method.

The "salts" of the 1-substituted imidazoles are standard pharmaceutically acceptable acid addition salts such as those enumerated in U.S. Pat. No. 4,078,071. The term "clinically asymptomatic of microbial infection" means that the subject does not have a fungal, bacterial or protozoal infection which is readily apparent to the skilled medical practitioner.

It has been found that a wide variety of classes of known 1-substituted imidazole compounds previously described as exhibiting anti-fungal, anti-bacterial and/or anti-protozoal activity, exhibit the aforementioned remarkable spermatostatic and spermatocidal effects, both in the male and female mammal. Illustrative of the classes of 1-substituted imidazoles forming a part of the present invention are those represented by the following general structural formulas (as well as pharmaceutically acceptable acid addition salts thereof) and/or described in the issued patents listed hereinbelow:

(a) Compounds of the formula

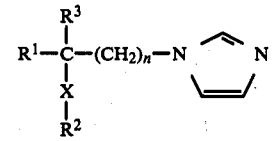

wherein $R^1$ and $R^2$ are each independently alkyl (1–12), alkenyl (1–12), substituted or unsubstituted phenyl or phenyl lower alkyl (1–4), substituted or unsubstituted phenyl lower alkenyl (1–4) wherein "substituted" contemplates substitution by one or more lower alkyl (1–4), halo, lower alkoxy (1–4), trifluoromethyl, nitro or cyano groups;

$R^3$ is hydrogen or lower alkyl (1–4); X is oxygen or sulfur; and n is an integer of from 1 to 4; especially those described in U.S. Pat. Nos. 3,717,655, 3,839,574, 3,658,813, 4,055,652, 4,078,071, 4,045,568, 4,059,705, and 4,123,542. Inclusive of representative compounds within this class are sulconazole, i.e. 1-[2-(4-chlorobenzylthio)-2-(2,4-dichlorophenyl)ethyl]imidazole, miconazole, i.e. 1-[2-(2,4-dichlorobenzyloxy)-2-(2,4-dichlorophenyl)ethyl]imidazole, econazole, i.e., 1-[2-(4-chlorobenzyloxy)-2-(2,4-dichlorophenyl)ethyl]imidazole, orconazole, i.e., 1-[2-(2,6-dichlorobenzyloxy)-2-(4-chlorphenyl)ethyl]imidazole, and R23979, i.e., 1-[2-allyloxy-2-(2,4-dichlorophenyl)ethyl]imidazole.

(b) 1-Substituted imidazole ketals such as those described in U.S. Pat. Nos. 3,575,999, 3,793,453, 3,936,470, 4,101,664, 4,101,665, 4,101,666 and Belgian Pat. No. 863,382. Compounds especially noteworthy within this group are parconazole, i.e., 1-[2-(2,4-dichlorophenyl)-4-[(2-propynyloxy)methyl]-1,3-dioxolan-2-ylmethyl]-1H-imidazole; ketoconazole, i.e., 1-acetyl-4-[4-[2-(2,4-dichlorophenyl)-2-(1H-imidazol-1-ylmethyl)-1,3-dioxolan-4-yl-methoxy]-phenyl]piperazine; and R34000, i.e. 1-[2-(2,4-dichlorophenyl)-4-[4-phenylphenoxy)methyl]-1,3-dioxolan-2-ylmethyl]-1H-imidazole.

(c) 1-Substituted imidazole diethers (thioethers) such as those in U.S. Pat. Nos. 4,036,970, 4,036,973, and 4,036,974.

(d) 1-Substituted imidazole ester derivatives such as those in U.S. Pat. Nos. 4,038,409 and 4,039,677.

(e) Heteroaryl 1-substituted imidazole derivatives such as those described in Belgian Pat. Nos. 841,309 and 849,012. Particularly noteworthy compounds in this group are tioconazole, i.e., 1-[2-(2-chloro-3-thienylmethoxy)-2-(2,4-dichlorophenyl)ethyl]imidazole and its sulfur counterpart, i.e., 1-[2-(2-chloro-3-thienylmethylthio)-2-(2,4-dichlorophenyl)ethyl]imidazole;

(f) Triarylmethyl substituted imidazoles such as those described in U.S. Pat. No. 3,705,172, South African Pat. Nos. 6,805,392 and 6,900,039. The compound clotrimazole, 1-[(2-chlorophenyl)diphenylmethyl]imidazole, is especially noteworthy in this group.

(g) Other miscellaneous 1-substituted imidazoles such as those described in U.S. Pat. Nos. 3,927,017, 3,991,201, 4,057,545, Belgian Pat. Nos. 827,870, 838,298, and Belgian Pat. No. 804,092, German OLS No. 2,348,663, Belgian Pat. Nos. 820,703 and 778,793, U.S. Pat. Nos. 3,812,142 and 3,903,287, Belgian Pat. Nos. 835,953, 963,851, 857,522 and 816,954, German OLS No. 2,632,602, U.S. Pat. Nos. 3,821,394, 3,826,836, 3,870,726, 3,985,766, 3,711,487, 3,910,936, 3,887,556, 3,709,901, and 3,796,704, Belgian Pat. Nos. 856,428, 836,924, 857,431, 845,433, 857,836, 858,113, 847,001, 848,004 and 838,298, German OLS Nos. 2,805,227, and 2,802,496, and U.S. Pat. Nos. 4,113,465 and 4,036,975. All of the aforementioned patent citations in (a)-(g) are hereby incorporated by reference herein.

An especially useful group of compounds are those described under (a) above. Most useful are those showing the following combinations of substituents:

(i) $R^1$ is alkyl, $R^2$ is alkyl, substituted or unsubstituted phenyl, substituted or unsubstituted benzyl, $R^3$ is hydrogen and n is 1 or 2;

(ii) $R^1$ is substituted or unsubstituted phenyl, $R^2$ is substituted or unsubstituted benzyl, $R^3$ is hydrogen and n is 1;

(iii) $R^1$ is substituted or unsubstituted phenethyl, $R^2$ is substituted or unsubstituted phenyl, $R^3$ is hydrogen and n is 1; and (iv) $R^1$ is substituted or unsubstituted benzyl, $R^2$ is substituted or unsubstituted phenyl or benzyl, $R^3$ is hydrogen and n is 2.

One especially preferred group of compounds are those wherein $R^1$ is alkyl having from 3 to 7 carbon atoms, more preferably from 4 to 6 carbon atoms, and most preferably 5 carbon atoms, $R^2$ is substituted or unsubstituted phenyl, preferably phenyl substituted with halo or lower alkyl, and n is 2.

A second especially preferred group of compounds are those wherein $R^1$ is alkyl having from 4 to 8 carbon atoms, $R^2$ is substituted or unsubstituted benzyl and n is 1.

In the practice of the method of contraception in the female mammal utilizing the aforementioned 1-substituted imidazoles, it is expedient to administer the active compound in a suitable formulation intravaginally, prior to coitus. The preferred dosage range of active ingredient is from about 0.001 to about 0.1 grams of active substance for each vaginal administration for a typical adult human subject. For smaller mammals the amount would be reduced correspondingly.

For administration according to the aforementioned method one would employ a pharmaceutical composition standard in the art for intravaginal spermatostatic or spermatocidal type contraception including for example vaginal suppositories, vaginal tablets, vaginal creams, vaginal spray-foams, vaginal soluble waffles, vaginal sponges, and the like, as well as slow release formulations such as implants. Each of these compositions would contain an effective amount of the active ingredient in a pharmaceutically acceptable non-toxic carrier or excipient normally employed for such formulations. Typical excipients for solid formulations are, for example, starch, glucose, lactose, mannitol, magnesium stearate, talc, cellulose, magnesium carbonate, sodium bicarbonate, citric acid, and the like. For semi-solid formulations such as suppositories, excipients such as polyalkylene glycols, modified vegetable oils or soft gelatin capsules containing, e.g., vegetable oil, mineral oil or polyalkylene glycol formulations may be used. For liquid or liquid-type formulations such as creams, jellies, foams, and the like, there may be used water, saline solution, aqueous dextrose, glycerol, higher alcohols, mineral oil, lanolin, gums of vegetable origin, polyalkylene glycols and propellants such as those of the Freon type. The compositions may contain between about 0.1 and 10.0 percent by weight of the active ingredient, preferably between about 0.5 and 2.0 percent by weight, and may, if desired, contain other active ingredients. Additionally, the above compositions may be utilized in conjunction with other contraceptive methods such as barrier methods, e.g. the condom or diaphragm.

In the further practice of the present invention contraception is effected by administering, orally or parenterally, to a male mammal, prior to coitus, a spermatostatically effective amount of a 1-substituted imidazole or salt thereof. An effective dosage range for the practice of such method is between about 0.1 and about 10.0 mg active ingredient per kilogram body weight per day either in one dose (preferred) or distributed over several doses. The exact regimen will necessarily be dependent upon the particular compound employed, the nature of the subject, and the like. As a rule, to ensure complete lack of motility of the spermatic cells, it is prudent to administer the compound to the male mammal at least 24 hours prior to coitus, preferably daily for a period of 3 to 7 days prior to coitus.

Another method of parenteral administration is via a slow-release subcutaneous implant type of formulation such as those generally known in the art, particularly those that are biosoluble or biodegradable. In this method only one administration need be made to supply active ingredient for an extended period, e.g. one month. See, e.g., U.S. Pat. Nos. 3,279,996 and 4,096,239.

In another aspect the present invention is concerned with pharmaceutical compositions for oral or parenteral administration to a male mammal suitable for practice of the contraceptive method described above. Again, such pharmaceutical compositions will contain a spermatostatically effective amount of the active ingredient in a pharmaceutically acceptable non-toxic carrier or excipient. Typical formulations for oral administration include solid dosage forms such as tablets, capsules and powders as well as liquid dosage forms such as solutions, suspensions, and the like. For parenteral administration one of the aforementioned liquid dosage forms would typically be employed or a solid or semi-solid implant would be used. Typical excipients for solid formulations include, for example, magnesium stearate, starch, lactose, gelatin, and the like; for liquid formulations there may be mentioned, for example, polyalkylene glycols, water, oils of vegetable origin and low boiling solvents such as isopropanol and hydrogenated naphthalenes.

The following examples are illustrative of the methods and compositions of the present invention. They should not be construed as limitative thereof in any manner.

EXAMPLE 1

The following illustrates formulations for vaginal administration. The specific active ingredient utilized is 1-[3-(4-chlorophenylthio)octyl]imidazole oxalate, although any 1-substituted imidazole referred to above may be utilized.

(a) Water soluble vaginal cream

| Ingredients | % w/w |
|---|---|
| Active ingredient | 1.0 |
| Cetostearyl alcohol | 12.0 |
| Polyoxyethylene sorbitan monostearate | 2.0 |
| Sorbitan monostearate | 2.0 |
| Mineral oil | 2.0 |
| Propylene glycol | 4.0 |
| Benzyl alcohol | 1.0 |
| Butylated hydroxyanisole | 0.01 |
| Purified water qs ad | 100.0 |

For each application approximately 0.5 grams of the cream are vaginally administered to an adult human female with a suitable syringe.

(b) Vaginal jelly

| Ingredients | % w/w |
|---|---|
| Active ingredient | 1.0 |
| Glycerine | 8.0 |
| Gum acacia | 1.0 |
| Tragacanth | 2.5 |
| Methyl paraaminobenzoate | 0.2 |
| Purified water qs ad | 100.0 |

For each application approximately 0.5 grams of the jelly are vaginally administered to an adult human female with a suitable syringe.

(c) Vaginal suppository

| Ingredients | % w/w |
|---|---|
| Active ingredient | 1.0 |
| Polyethylene glycol 4000 | 20.0 |
| Butylated hydroxyanisole | 0.01 |
| Polyethylene glycol 1000 qs ad | 100.0 |

The above materials are formed into suppositories of about 3 grams each.

(d) Effervescent vaginal tablets—composition of a 2 gram tablet

| Ingredients | |
|---|---|
| Active ingredient | 0.020 g |
| Anhydrous citric acid | 0.7 g |
| Sodium bicarbonate | 0.3 g |
| Polyethylene glycol 6000 | 0.4 g |
| Lactose qs | 2 g |

(e) Vaginal spray-foam—composition of 100 g batch

| Ingredients | |
|---|---|
| Active ingredient | 1 g |
| Polyethylene glycol 6000 | 2 g |
| Non-ionic emulsifying agent | 2 g |
| Purified water | 85 g |
| Freon 12/114 (70:30) | 10 g |

For each application approximately 0.5 grams of the foam are vaginally administered.

(f) Vaginal soluble waffle—composition for a 0.4 gram waffle

| Ingredients | |
|---|---|
| Active ingredient | 0.004 g |
| Starch | 0.040 g |
| Water soluble lanolin qs | 0.40 g |

EXAMPLE 2

The following pharmaceutical compositions are representative of those which may be used for oral or parenteral administration to a male mammal. The active ingredient illustrated is the same as for that in Example 1 although any active ingredient referred to above may be utilized.

(a) Oral formulation—tablet

| Ingredients | parts by weight |
|---|---|
| Active ingredient | 200 |
| Magnesium stearate | 3 |
| Starch | 30 |
| Lactose | 116 |
| Polyvinylpyrrolidone | 3 |

The above ingredients are combined and granulated using methanol as the solvent. The formulation is then dried and formed into tablets containing 200 milligrams of active compound with an appropriate tableting machine.

(b) Parenteral formulation for IV use—composition of 100 ml of solution

| Ingredients | |
|---|---|
| Active ingredient | 2.0 g |
| Propylene glycol | 20 g |
| Polyethylene glycol | 20 g |
| Tween 80 | 1 g |
| 0.9% Saline solution qs | 100 ml |

The active ingredient is dissolved in propylene glycol, polyethylene glycol 400 and Tween 80. A sufficient quantity of 0.9% saline solution is then added with stirring to provide 100 ml of the IV solution which is filtered through a 0.2 micron membrane filter and packaged under sterile conditions.

(c) Implant formulation

| Ingredients | % (w/w) |
|---|---|
| Active ingredient | 2.0 |
| Polyethylene glycol 6000 | 5.0 |

| Ingredients | % (w/w) |
|---|---|
| Cholesterol qs | 100.0 |

The ingredients are mixed and compressed into pellets of approximately 2 mm (diameter) × 8 mm.

EXAMPLE 3

The following example illustrates the spermatostatic and spermatocidal activity of a large variety of 1-substituted imidazole derivatives when contacted directly with semen. This is representative of the effect for female contraception.

Semen is collected from a male dog and divided into aliquots. The test compound is dissolved in distilled water at concentrations of 1, 10 and 100 micrograms/ml. These solutions of test compound are mixed with semen in the ratio of 1 part test solution to 3 parts semen (v/v). They are then examined microscopically (a) immediately and (b) after 1 hour. In the following chart the results are tabulated for a large number of 1-substituted imidazole derivatives. The parameters measured were minimum concentration of test compound (after admixture of test solution with semen) necessary to achieve (i) instant kill, (ii) greater than 75% kill after one hour, and (iii) zero motility after one hour.

| Test Compound | Minimum dosage (µg/ml) causing | | |
|---|---|---|---|
| | Instant Kill | 75% kill (1 hour) | Zero Motility (1 hour) |
| 1-[2-(4-chlorobenzylthio)-2-(2,4-dichlorophenyl)ethyl]imidazole nitrate | 25 | — | 2.5 |
| 1-[2-(2,6-dichlorophenylthio)-4-(4-chlorophenyl)n-butyl]imidazole nitrate | — | 25 | 2.5 |
| 1-[2-(2,4-dichlorobenzyloxy)-2-(2,4-dichlorophenyl)-ethyl] imidazole nitrate | — | 25 | 2.5 |
| 1-[2,3-bis(4-chlorophenylthio)-n-propyl] imidazole nitrate | 25 | — | 2.5 |
| 1-[2-n-heptylthio-2-(2,4-dichlorophenyl)ethyl] imidazole nitrate | — | 25 | 2.5 |
| 1-[2-(ethoxythiocarbonylthio)-2-(2,4-dichlorophenyl)ethyl]imidazole oxalate | — | 25 | 2.5 |
| 1-[2-(4-chlorobenzylsulfinyl)-2-(2,4-dichlorophenyl)ethyl]imidazole nitrate | — | — | 25 |
| 1-[2-(4-chlorobenzoylthio)-2-(2,4-dichlorophenyl)ethyl]imidazole nitrate | — | — | 25 |
| 1-[3-(n-octylthio)octyl]imidazole oxalate | 25 | 2.5 | <2.5 |
| 1-[3-(4-chlorophenylthio)octyl]imidazole oxalate | 25 | — | 0.25 |
| 1-[2-(4-methoxybenzylthio)-2-(2,4-dichlorophenyl)ethyl]imidazole nitrate | — | 25 | 2.5 |
| 1-[2-(2,4-dichlorobenzyloxy)-4-(4-chlorophenyl)-n-butyl]imidazole nitrate | — | 25 | 2.5 |
| 1-[(2-chlorophenyl)diphenylmethyl]imidazole | — | — | 25 |
| 1-[2-(4-chlorobenzyloxy)-2-(2,4-dichlorophenyl)ethyl]-imidazole nitrate | 25 | — | 0.25 |
| 1-(3-n-dodecylthio-n-butyl)-imidazole oxalate | — | 25 | 2.5 |
| 1-[3-(4-chlorobenzylthio)-n-octyl]imidazole nitrate | — | 25 | 2.5 |
| 1-(3-n-hexyloxy-n-octyl)-imidazole oxalate | 25 | — | 2.5 |
| 1-(2-n-octylthio-n-octyl)-imidazole oxalate | — | 25 | 2.5 |
| 1-[3-(4-chlorobenzyloxy)-n-octyl]imidazole oxalate | 25 | 2.5 | 0.25 |
| 1-[3-(2,4-dichlorobenzyloxy)-n-octyl]imidazole oxalate | 25 | — | 2.5 |
| 1-[2-(4-chlorophenylthio)-4-(4-chlorophenyl)-n-butyl]-imidazole nitrate | — | 2.5 | <2.5 |
| 1-[3-(2-chlorobenzylthio)-4-(4-chlorophenyl)-n-butyl]-imidazole nitrate | 25 | — | 2.5 |
| 1-[2-(2,4-dichlorobenzyloxy)-n-octyl]imidazole oxalate | 25 | 2.5 | 0.25 |
| 1-[2-(4-chlorobenzylthio)-n-octyl]imidazole nitrate | 25 | — | 0.25 |
| 1-[3-(2,4-dichlorophenylthio)-n-heptyl]imidazole oxalate | 25 | — | 0.25 |
| 1-[2-(2,4-dichlorophenylthio)-2-methyl-n-hexyl]-imidazole nitrate | 25 | — | 2.5 |
| 1-(2-ethylthiotetradecyl)-imidazole oxalate | — | 2.5 | <2.5 |
| 1-[3-(4-chlorophenylthio)-3-(2,4-dichlorophenyl)-n-propyl]imidazole | — | 25 | <2.5 |
| 1-[4-(4-chlorophenylthio)-4-(2,4-dichlorophenyl)-n-butyl]imidazole oxalate | — | 25 | 2.5 |
| 1-[3-(4-tert-butylphenylthio)-n-octyl]imidazole oxalate | 25 | — | 0.25 |
| 1-[4-(4-chlorobenzyloxy)-4-(2,4-dichlorophenyl)-n-butyl]imidazole nitrate | — | — | 25 |
| 1-[3-(n-hexylthio)-3-(2,4-dichlorophenyl)-n-propyl]-imidazole oxalate | 25 | — | 2.5 |
| 1-[2-(4-chlorobenzylthio)-3-(n-butylthio)-n-propyl]-imidazole | — | 25 | <2.5 |
| 1-[4-(2,4-dichlorobenzyloxy)-4-(4-chlorophenyl)-n-butyl]imidazole nitrate | — | 25 | 25 |
| 1-(3-n-decyloxy-cyclohexyl-n-propyl)imidazole oxalate | — | — | 0.25 |

EXAMPLE 4

The following experiment illustrates the spermatostatic effect of a typical 1-substituted imidazole derivative, sulconazole nitrate, 1-[2-(4-chlorobenzylthio)-2-(2,4-dichlorophenyl)ethyl]imidazole nitrate, when administered orally at various dosages to male dogs (approximately 10 kg) daily for a period of 6 weeks. After the 6 week treatment period semen was collected from each dog. The entire ejaculate, including both initial spermatozoa rich and prostatic secretion fractions were collected from the dogs into pre-warmed (37° C.) collection tubes. Immediately after collection the tubes were sealed and placed in a 37° C. water bath. After 60 minutes from collection the ejaculate was well mixed by repeated inversion. A drop was withdrawn and placed on a pre-warmed slide and the motility of spermatozoa were immediately assessed microscopically. Motility was scored on a scale of 0 to 5, the high score representing high motility. Motility was assessed as the total impression of motility within the optical field rather than by assessing motility of individual spermatozoa. The results were as follows:

| Group No. | Dosage (mg/dog/day) | Motility Rating (average for group) at 60 min. |
|---|---|---|
| 1 | 0 | 3.7 |
| 2 | 100 | 1.7 |
| 3 | 330 | 0 |
| 4 | 1000 | 0 |

The formulations utilized for the above study were as follows:

| Ingredient | wt. (mg) per capsule | | |
|---|---|---|---|
| Sulconazole nitrate | 100 | 330 | 250 |
| NuTab ® (SuCrest) compressible sugar | 280 | 220 | 300 |
| Polyvinylpyrrolidone | 7.6 | 11 | 11 |
| Capsule size | No. 1 | No. 0 | No. 0 |

The ingredients were combined and granulated using methanol as the solvent. The formulation is then dried and the capsules filled. For the 1000 mg/dog/day dose, four 250 mg capsules were utilized.

What is claimed is

1. A method of contraception in a male mammal comprising administering to a subject clinically asymptomatic of microbial infection, prior to coitus, a spermatostatically effective amount of a 1-substituted imidazole of the formula

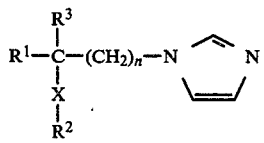

wherein $R^1$ and $R^2$ are each independently alkyl (1–12), alkenyl (1–12), substituted or unsubstituted phenyl, substituted or unsubstituted phenyl lower alkyl (1–4), or substituted or unsubstituted phenyl lower alkenyl (1–4), wherein substituted with reference to phenyl refers to phenyl substituted by one or more lower alkyl (1–4), halo, lower alkoxy (1–4), trifluoromethyl, nitro or cyano groups; $R^3$ is hydrogen or lower alkyl (1–4); X is oxygen or sulfur; n is an integer of from 1 to 4; or a pharmaceutically acceptable acid addition salt thereof.

2. The method of claim 1 wherein $R^1$ is alkyl, $R^2$ is alkyl or substituted or unsubstituted phenyl or benzyl, $R^3$ is hydrogen and n is 1 or 2.

3. The method of claim 2 wherein $R^1$ is alkyl (3–7), $R^2$ is substituted or unsubstituted phenyl and n is 2.

4. The method of claim 1 wherein said compound is 1-[2-(4-chlorobenzylthio)-2-(2,4-dichlorophenyl)ethyl]-imidazole and the pharmaceutically acceptable acid addition salts thereof.

5. The method of claim 1 wherein said compound is 1-[2-(2,4-dichlorobenzyloxy)-2-(2,4-dichlorophenyl)-ethyl]imidazole and the pharmaceutically acceptable acid addition salts thereof.

6. The method of claim 1 wherein said compound is 1-[2-(4-chlorobenzyloxy)-2-(2,4-dichlorophenyl)ethyl]-imidazole and the pharmaceutically acceptable acid addition salts thereof.

7. The method of claim 1 wherein said compound is 1-[2-(2,6-dichlorobenzyloxy)-2-(4-chlorophenyl)ethyl]-imidazole and the pharmaceutically acceptable acid addition salts thereof.

8. The method of claim 1 wherein said compound is 1-[2-(allyloxy)-2-(2,4-dichlorophenyl)ethyl]imidazole and the pharmaceutically acceptable acid addition salts thereof.

9. The method of claim 1 wherein said compound is 1-[2-(2,6-dichlorophenylthio)-4-(4-chlorophenyl)-n-butyl]imidazole and the pharmaceutically acceptable acid addition salts thereof.

10. The method of claim 3 wherein said compound is 1-[3-(4-chlorophenylthio)-n-octyl]imidazole and the pharmaceutically acceptable acid addition salts thereof.

11. The method of claim 3 wherein said compound is 1-[3-(4-tert-butylphenylthio)-n-octyl]imidazole and the pharmaceutically acceptable acid addition salts thereof.

12. The method of claim 2 wherein $R^1$ is alkyl (4–8), $R^2$ is substituted or unsubstituted benzyl and n is 1.

13. The method of claim 12 wherein said compound is 1-[2-(2,4-dichlorobenzyloxy)-n-octyl]imidazole and the pharmaceutically acceptable acid addition salts thereof.

14. A method of contraception in a male mammal comprising administering to a subject clinically asymptomatic of microbial infection, prior to coitus, a spermatostatically effective amount of 1-[2-(2,4-dichlorophenyl)-4-[(4-phenylphenoxy)methyl]-1,3-dioxolan-2-ylmethyl]-1H-imidazole or a pharmaceutically acceptable acid addition salt thereof.

15. A method of contraception in a male mammal comprising administering to a subject clinically asymptomatic of microbial infection, prior to coitus, a spermatostatically effective amount of 1-[2-(2,4-dichlorophenyl)-4-[(2-propynyloxy)methyl]-1,3-dioxolan-2-ylmethyl]-1H-imidazole or a pharmaceutically acceptable acid addition salt thereof.

16. A method of contraception in a male mammal comprising administering to a subject clinically asymptomatic of microbial, infection prior to coitus, a spermatostatically effective amount of 1-acetyl-4-[4-[2-(2,4-dichlorophenyl)-2-(1H-imidazol-1-ylmethyl)-1,3-dioxolan-4-ylmethyoxy]-phenyl]piperazine or a pharmaceutically acceptable acid addition salt thereof.

17. A method of contraception in a male mammal comprising administering to a subject clinically asymptomatic of microbial infection, prior to coitus, a spermatostatically effective amount of 1-[2-(2-chloro-3-thienylmethoxy)-2-(2,4-dichlorophenyl)-ethyl]imidazole or a pharmaceutically acceptable acid addition salt thereof.

18. A method of contraception in a male mammal comprising administering to a subject clinically asymptomatic of microbial infection, prior to coitus, a spermatostatically effective amount of 1-[2-(2-chloro-3-thienylmethylthio)-2-(2,4-dichlorophenyl)-ethyl]imidazole or a pharmaceutically acceptable acid addition salt thereof.

19. A method of contraception in a male mammal comprising administering to a subject clinically asymptomatic of microbial infection, prior to coitus, a spermatostatically effective amount of 1-[(2-chlorophenyl)-diphenylmethyl]imidazole or a pharmaceutically acceptable acid addition salt thereof.

* * * * *